(12) United States Patent
Marshall et al.

(10) Patent No.: US 8,394,814 B2
(45) Date of Patent: Mar. 12, 2013

(54) METHOD OF PURIFYING CRUDE NOSCAPINE

(75) Inventors: Benjamin M. Marshall, St. Charles, MO (US); Keith G. Tomazi, Florissant, MO (US)

(73) Assignee: Mallinekrodt LLC, Hazelwood, MO (US)

( * ) Notice: Subject to any disclaimer, the term of this patent is extended or adjusted under 35 U.S.C. 154(b) by 719 days.

(21) Appl. No.: 12/586,850

(22) Filed: Sep. 29, 2009

(65) Prior Publication Data

US 2010/0081822 A1    Apr. 1, 2010

Related U.S. Application Data

(60) Provisional application No. 61/194,677, filed on Sep. 30, 2008.

(51) Int. Cl.
*A61K 31/44* (2006.01)
*B01D 11/02* (2006.01)

(52) U.S. Cl. .................................... 514/282; 210/773

(58) Field of Classification Search ............... 514/282; 210/773
See application file for complete search history.

(56) References Cited

FOREIGN PATENT DOCUMENTS

| WO | WO 2005/123743 | 12/2005 |
|---|---|---|
| WO | WO 2007/120538 | 10/2007 |

OTHER PUBLICATIONS

Landen et al., "Noscapine Crosses the Blood-Brain barrier and Inhibits Glioblastoma Growth", Clinical Cancer Research, vol. 10, Aug. 1, 2004, pp. 5187-5201.
Montgomery et al., "The Rhoeadine Alkaloids", Journal of Natural Products, 1983, 46(4), pp. 441-453.
Heumann; The Manufacture of alkaloids from opium; Bulletin on Narcotics, 9(2); 1957; pp. 34-40; XP 002345736.
Ramanthan; Recovery, separation and purification of narcotine and papaverine from Indian opium; Bulletin on Narcotics; 33(1); 1981; pp. 55-64; XP 009089931.

*Primary Examiner* — John Mabry

(57) ABSTRACT

The invention provides a method for separating noscapine from an opium source without substantially changing the color of the noscapine.

20 Claims, 12 Drawing Sheets

Noscapine

Glaudine

Epiglaudine

Oreodine

Morphine

Oripavine

Papaverine

Thebaine

Codeine

Cryptopine

Narcotoline

Nor-Noscapine

METHOD OF PURIFYING CRUDE NOSCAPINE

FIELD OF THE INVENTION

The present invention provides a method for separating noscapine from an opium source comprising at least one impurity that undergoes an irreversible color change when exposed to a pH of less than about 5.

BACKGROUND OF THE INVENTION

Noscapine, CAS # 128-62-1, is used in cough suppressants in Japan and throughout the Asian continent. Noscapine is a natural product found in opium that can cross the blood-brain barrier to exert its effect upon the central nervous system, resulting in cough suppression. In addition, noscapine has been shown in animal studies to reduce tumor growth, and exploratory research into the use of noscapine as an anti-tumor agent is ongoing.

Noscapine, as shown in FIG. 1, may be extracted from crude opium. In addition, other substances such as morphine may be present in the crude opium. Morphine is a controlled substance subject to governmental control in many localities, and the amount of crude opium available to a particular producer of noscapine may be limited by the amount of morphine in the crude opium. Therefore, the manufacturing capacity of the noscapine producer using crude opium as a noscapine source may be limited by governmental rules related to the morphine content of the crude opium.

To address this limitation, noscapine manufacturers have turned to alternative sources of noscapine, such as poppy straw, which is a mixture of stems and capsules from the harvested opium poppy, *Papaver somniferum*. Depending on the particular strain of poppy and the post-harvest processing of the poppy straw, the poppy straw may have a much higher proportion of noscapine content relative to morphine content.

However, poppy straw may additionally contain a number of impurities such as papaverrubine compounds. Papaverrubine compounds may irreversibly transform into red iminium salts under acidic conditions, as shown in FIG. 2. When present in purified noscapine products, the red iminium salts impart an undesirable reddish color to the noscapine product. Unfortunately, most current methods of noscapine extraction and purification involve dissolving the crude noscapine source into an acidic solution.

A need exists to develop a method of separating noscapine from an opium source that may contain papaverrubines or other impurities that undergo irreversible color changes when exposed to acidic process conditions.

SUMMARY OF THE INVENTION

One aspect of the present invention provides a method for separating noscapine (CAS # 128-62-1) from an opium source comprising at least one impurity that undergoes an irreversible color change when exposed to a pH of less than about 5. The method comprises contacting the opium source with a first solvent that substantially causes the dissolution of noscapine, forming a reaction mixture comprising a pH of greater than about 5. The method further comprises contacting the reaction mixture with a second solvent that reduces the solubility of the noscapine in the reaction mixture without substantially changing the solubility of the impurity such that the noscapine recrystallizes, thereby separating the noscapine from the impurity in a manner that does not cause an irreversible color change in the impurity.

Another aspect of the invention provides a method for separating noscapine (CAS # 128-62-1) from an opium source comprising at least one impurity that undergoes an irreversible color change when exposed to a pH of less than about 5. The method comprises contacting the opium source with a solvent mixture, forming a slurry with a pH of greater than about 5.

Another aspect of the present invention provides a method for separating noscapine (CAS # 128-62-1) from an opium source comprising at least one impurity that undergoes an irreversible color change when exposed to a pH of less than about 5. The method comprises contacting the opium source with a first solvent selected from the group consisting of acetone, acetonitrile, and combinations thereof to form a reaction mixture having a pH of greater than about 5. The method further comprises contacting the reaction mixture with water such that the noscapine recrystallizes, thereby separating the noscapine from the impurity.

Another aspect of the invention provides a method for separating noscapine (CAS # 128-62-1) from an opium source comprising at least one impurity that undergoes an irreversible color change when exposed to a pH of less than about 5. The method comprises contacting the opium source with a solvent mixture comprising a first solvent selected from the group consisting of acetone, acetonitrile, and combinations thereof, and a second solvent comprising water, to form a slurry having a pH of greater than about 5.

Other aspects and features of the invention are described in more detail below.

DETAILED DESCRIPTION OF THE INVENTION

(I) Overview

Figure 1:
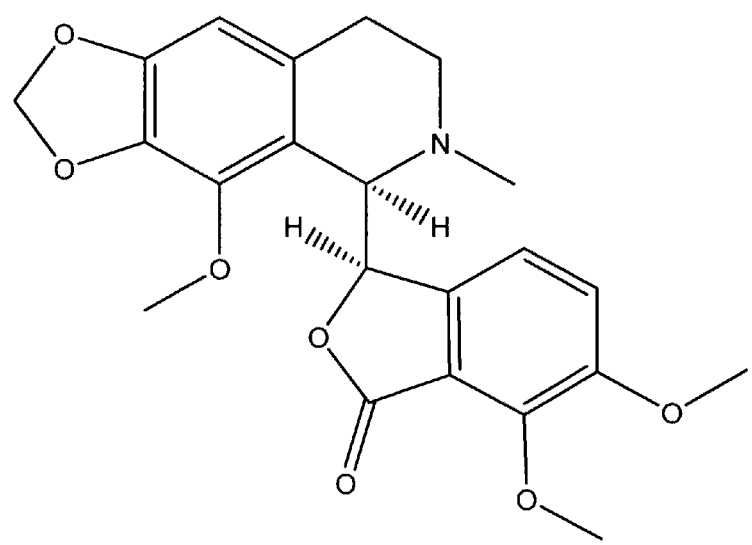
FIG. 1 is a chemical diagram of noscapine, CAS # 128-62-1.
Figure 2:
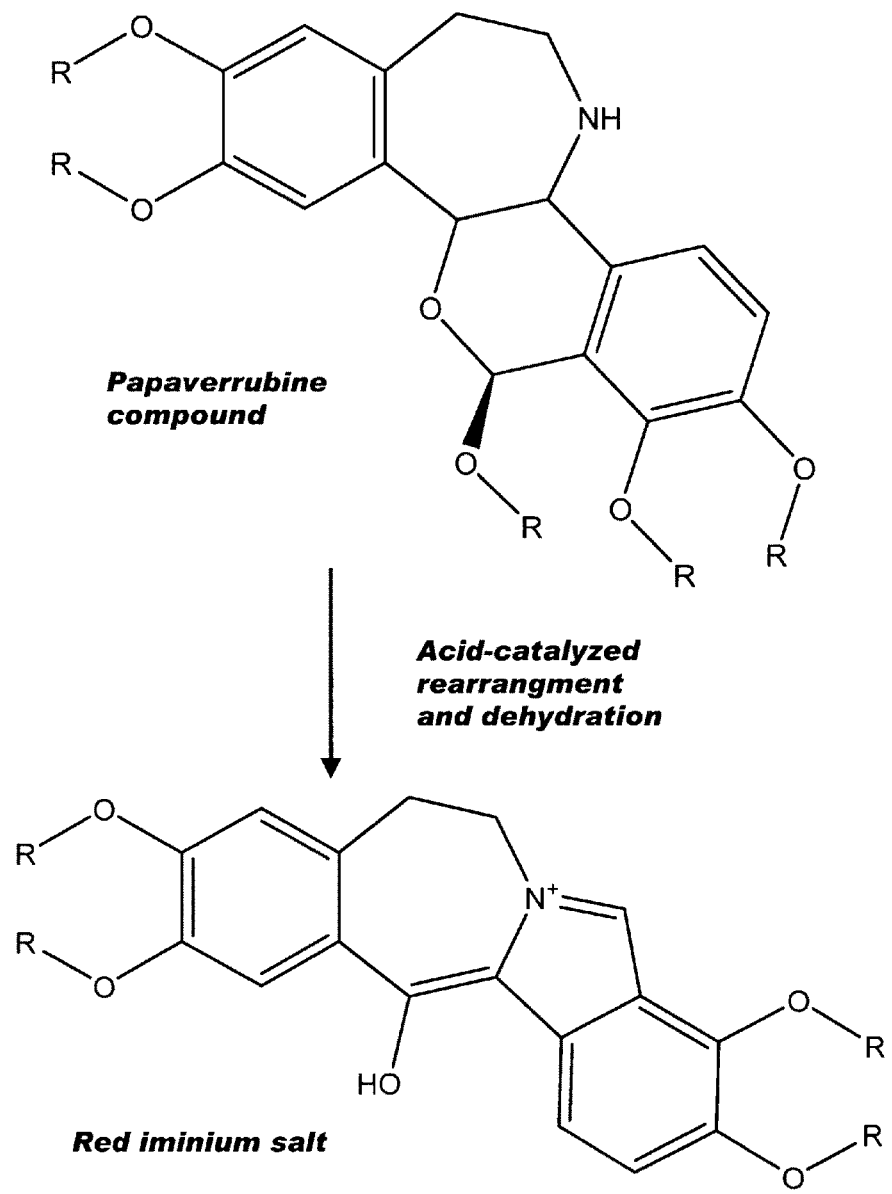
FIG. 2 is an illustration of the conversion of a papaverrubine compound into a red iminium salt.

One aspect of the present invention provides a method for separating noscapine from an opium source. In particular, the opium source comprises at least one impurity that undergoes an irreversible color change when exposed to a pH of less than about 5. For example, papaverrubine compounds, an impurity present in some opium sources, undergo an irreversible conversion into red iminium salts in acidic conditions, as illustrated in FIG. 2. Without being bound to any particular theory, if an opium source containing papaverrubine impurities is purified under process conditions in which the pH is below about 5 at any point in the process, red iminium salts may form, resulting in purified noscapine with an undesired red or pink color.

The method comprises contacting the opium source with a first solvent that substantially causes the dissolution of noscapine to form a reaction mixture comprising a pH of greater than about 5. The first solvent dissolves the noscapine into solution at a pH above about 5, forming a reaction mixture that includes the dissolved noscapine and may also include any dissolved contaminants that are soluble in the first solvent. The dissolved contaminants may include the impurity that undergoes an irreversible color change when exposed to a pH of less than about 5.

The method further comprises contacting the reaction mixture with a second solvent that reduces the solubility of the noscapine in the reaction mixture without substantially changing the solubility of the impurity. Because the second solvent does not substantially change the solubility of the impurity in the reaction mixture, the impurity remains dissolved in the reaction mixture. However, because the saturation concentration of noscapine in the reaction mixture is reduced by the addition of the second solvent, noscapine crystals precipitate out of the reaction mixture until the concentration of dissolved noscapine remaining in the reaction mixture falls below saturation levels. The resulting noscapine crystals in most embodiments comprise a purity of at least 98% noscapine by weight, and comprise a yield at least 80% of the noscapine by weight of the opium source. The method may further comprise filtering the noscapine crystals out of the reaction mixture. The method may additionally comprise rinsing the filtered noscapine crystals with a rinse solvent.

Another aspect of the invention provides a method for separating noscapine from an opium source comprising at least one impurity that undergoes an irreversible color change when exposed to a pH of less than about 5. The method comprises contacting the opium source with a solvent mixture to form a slurry. The solvent mixture comprises a mixture of a solvent in which noscapine is highly soluble and a solvent in which noscapine is relatively insoluble. The concentration of noscapine in the slurry is at least ten-fold higher than the saturation limit for noscapine in the reaction mixture, so that the solvent mixture is washing the opium source, rather than dissolving the noscapine. The solubility of the noscapine in the solvent mixture, and the concentration of noscapine in the slurry affect the resulting purity and yield of the noscapine crystals resulting from the method. The method may further comprise heating the slurry to enhance the separation of the impurities from the noscapine. The method may further comprise filtering the noscapine crystals out of the slurry. The method may additionally comprise rinsing the filtered noscapine crystals with a rinse solvent.

A detailed description of the materials used in the methods of the present invention, including opium source, first solvents, second solvents, solvent mixtures, and rinse solvents are presented below and in the examples below. In addition, reaction conditions such as temperature and pH are presented below and in the examples below. Additional aspects of the present invention such as filtration, and rinsing are presented below and in the examples below.

(II) Opium Source

The opium sources from which noscapine is separated using the method of the present invention are produced using exudates from live poppy plants, or plant matter derived from the opium poppy *Papaver somniferum*. The opium sources contain varying amounts of narcotic alkaloids including morphine, codeine, oripavine, thebaine, papaverine, and noscapine. Opium sources that are suitable for the method of the present invention include opium, poppy straw, concentrated poppy straw, crude noscapine, and crude narcotine. Opium is the dried exudate from the seed pods of living opium plants. Poppy straw is a collection of stems and capsules of the harvested poppy plant, and concentrated poppy straw is poppy straw that has been previously processed in some way so as to remove some of the impurities or to extract one or more of the narcotic alkaloids from the poppy stem. Crude narcotine is a processed opiate source in which the noscapine content is relatively high compared to opium, poppy straw, or concentrated poppy straw.

(a) Noscapine Content

The noscapine content of the opium source may range from about 1% to about 99% by weight. The noscapine content may range from about 1% to about 5%, about 4% to about 10%, about 9% to about 15%, about 14% to about 20%, about 19% to about 25%, about 24% to about 30%, about 29% to about 35%, about 34% to about 40%, about 39% to about 45%, about 44% to about 50%, about 49% to about 55%, about 54% to about 60%, about 59% to about 65%, about 64% to about 70%, about 69% to about 75%, about 74% to about 80%, about 79% to about 85%, about 84% to about 90%, about 89% to about 95%, and about 94% to about 99% by weight. Preferably, the noscapine content of the opium source ranges from about 80% to about 99%

(b) Impurities

The opium source contains at least one impurity that undergoes an irreversible color change when exposed to a pH of less than about 5. In addition, the opium source may contain other impurities that may not change color under acidic conditions, but must be removed from the opium source nonetheless in order to produce a noscapine product of suitable purity.

(i) Impurities that Undergo Irreversible Color Change when Exposed to pH<5

Figure 3:
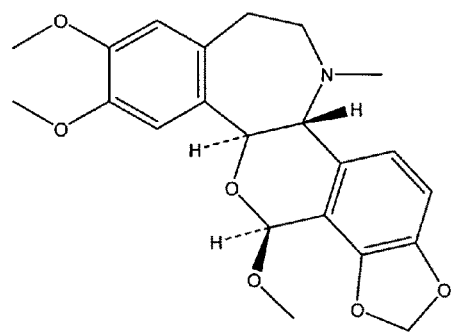
FIG. 3 shows chemical diagrams of three exemplary impurities found in some opium sources that undergo irreversible color changes when exposed to pH conditions of less than about 5.
Figure 3:
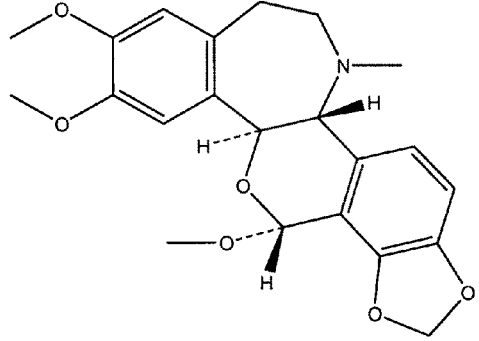
Figure 3:
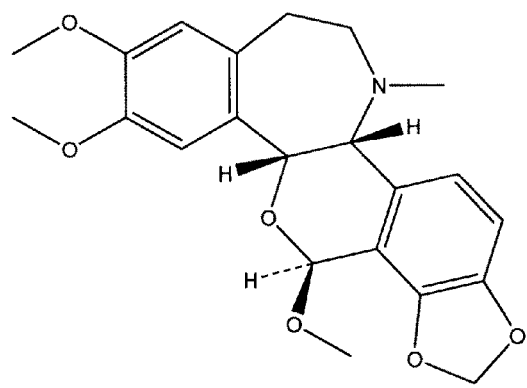
Figure 4A:
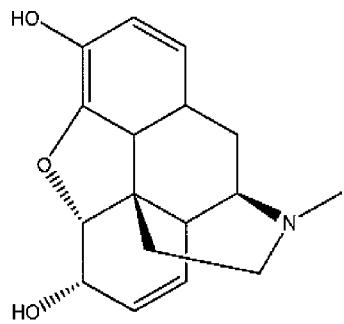
FIG. 4A shows chemical diagrams of six other exemplary impurities.
Figure 4A:
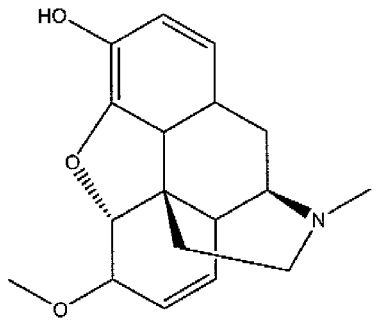
Figure 4A:
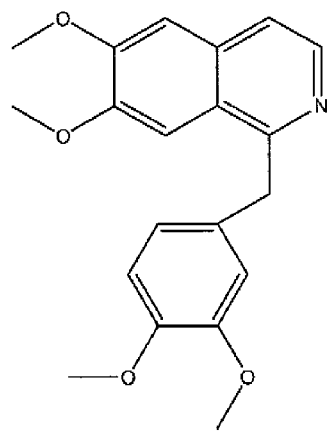
Figure 4A:
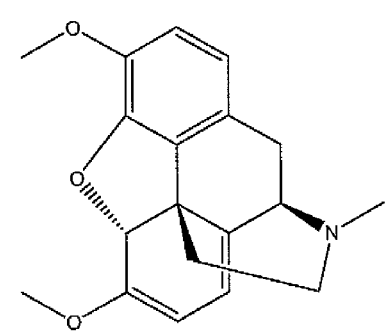
Figure 4A:
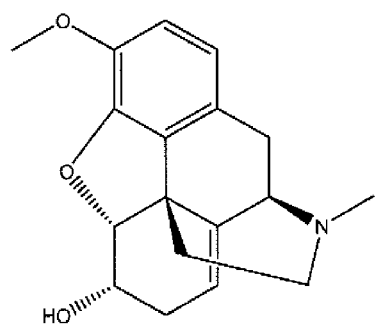
Figure 4A:
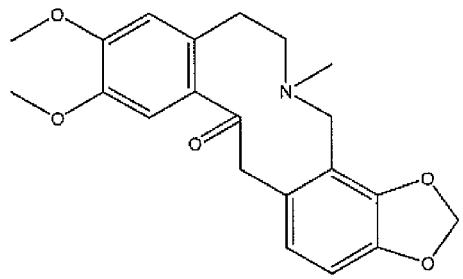
Figure 4B:
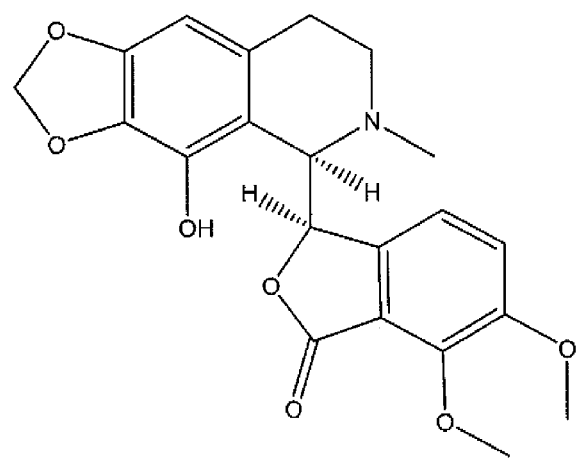
FIG. 4B shows chemical diagrams of two additional impurities found in some opium sources that do not undergo irreversible color changes when exposed to pH conditions of less than about 5.
Figure 4B:
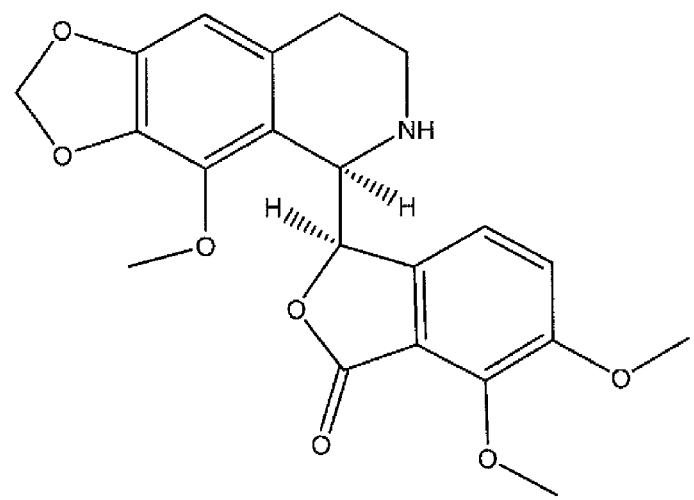

Impurities that undergo an irreversible color change when exposed to a pH of less than about 5 may include papaverrubines, glaudine, epiglaudine, oreodine, and combinations thereof. The papaverrubines may include papaverrubine A, papaverrubine B, papaverrubine C, papaverrubine D, papaverrubine E, papaverrubine F, papaverrubine G, epipapaverrubine G, papaverrubine H, and combinations thereof. Chemical diagrams of a representative sample of impurities that undergo irreversible color change when exposed to a pH of less than 5 are shown in FIG. 3.

(ii) Other Impurities

The opium source may also comprise impurities that do not necessarily undergo an irreversible color change when exposed to a pH of less than about 5. Although classified as impurities for the purposes of the method of the present invention, these impurities may have commercial value and other purification methods may be applied to render the impurities commercially useful products. Impurities that do not undergo an irreversible color change when exposed to a pH of less than about 5 may include morphine, oripavine, papaverine, thebaine, codeine, codeine, cryptopine, noscapine analogs, narcotoline, nor-noscapine, and combinations thereof. Chemical diagrams of a representative sample of the other impurities are shown in FIG. 4.

(III) First Solvent

In an aspect of the present invention, a first solvent may be initially contacted with the opium source, resulting in a reaction mixture. The reaction mixture comprises the first solvent and dissolved noscapine, along with any impurities that may also dissolve into the reaction mixture along with the noscapine. First solvents suitable for the method of the present invention possess the ability to dissolve noscapine in the opium source. In particular, the first solvent may have a high solubility for noscapine at a pH above about 5. In addition, the solubility of noscapine in the first solvent may significantly decrease after contact with the second solvent.

(a) Composition of First Solvent

Suitable first solvents include alkane and substituted alkane solvents, aromatic hydrocarbons, esters, ethers, ketones, and combinations thereof. In particular, suitable first solvents include acetonitrile, acetone, benzene, butanol, butyl acetate, t-butyl methylether, t-butyl methylketone, chlorobenzene, chloroform, chloromethane, cyclohexane, dichloromethane, dichloroethane, diethyl ether, ethyl acetate, fluorobenzene, heptane, hexanes, isobutylmethylketone, isopropyl acetate, methylethylketone, methylisobutylketone, methyltetrahydrofuran, pentyl acetate, n-propyl acetate, tetrahydrofuran, toluene, and combinations thereof. Preferably, the first solvent is acetonitrile, acetone, and combinations thereof.

The concentration of the first solvent is preferably 100% pure. However, the first solvent may be diluted by another solvent that is miscible with the first solvent. For example, acetonitrile may be diluted with water. The concentration of the first solvent may range from 100% to about 95%, from about 97% to about 93%, from about 95% to about 90%, from about 93% to about 87%, from about 90% to about 85%, from about 87% to about 83%, from about 85% to about 80%, from about 83% to about 77%, from about 80% to about 75%, from about 77% to about 73%, from about 75% to about 70%, from about 73% to about 67%, from about 70% to about 65%, from about 67% to about 63%, from about 65% to about 60%, from about 61% to about 55%, from about 56% to about 50%, from about 51% to about 45%, from about 46% to about 40%, from about 41% to about 35%, from about 36% to about 30%, from about 31% to about 25%, from about 26% to about 20%, from about 19% to about 15%, from about 16% to about 10%, from about 11% to about 5%, and from about 10% to about 1% by weight.

(b) Quantity of First Solvent

The quantity of first solvent that is contacted with the opium source may be selected so that essentially the entire amount of noscapine contained in the opium source is dissolved into the reaction mixture. However, in order to optimize the overall yield of the method of the present invention, the amount of noscapine dissolved in the reaction mixture may be near the saturation limit for noscapine in the first solvent. The absolute quantity of solvent that is suitable for the method of the present invention depends on the chemical properties of the first solvent used, and in particular depends upon the solubility of noscapine in the first solvent.

The quantity of first solvent contacted with the opium source may be selected to yield a noscapine concentration in the reaction mixture of 99% or less of the saturation concentration of noscapine in the first solvent. The quantity of first solvent contacted with the opium source may be selected to yield a noscapine concentration in the reaction mixture of 98% or less, 97% or less, 96% or less, 95% or less, 94% or less, 93% or less, 92% or less, 91% or less, 90% or less, 85% or less, 80% or less, 75% or less, 70% or less, 60% or less, 50% or less, 40% or less, 30% or less, 20% or less, or 10% or less of the saturation concentration of noscapine in the first solvent.

(c) Other Properties of First Solvent

The first solvent may have a pH ranging between 4 and about 5, about 4.5 and about 5.5, 5 and about 6, about 5.5 and about 6.5, 6 and about 7, about 6.5 and about 7.5, 7 and about 8, about 7.5 and about 8.5, 8 and about 9, about 8.5 and about 9.5, 9 and about 10, about 9.5 and about 10.5, 10 and about 11, and about 11.5 and about 12. The first solvent preferably has a pH of about 5 or above.

The first solvent should further be miscible with the second solvent of the method of the present method. In addition, the solubility of noscapine in the first solvent may be sensitive to changes in temperature, pH, or other conditions at which the method is performed. For example, the solubility of noscapine in acetonitrile more than doubles if the temperature of the acetonitrile is increased from 22° C. to 50° C., as described in the examples below.

(IV) Second Solvent

In an aspect of the present invention, a second solvent may be contacted with the reaction mixture that comprises the dissolved noscapine and the first solvent. Upon contact of the second solution with the reaction mixture, noscapine recrystallizes out of the reaction mixture. Second solvents suitable for the method of the present invention may possess the ability to decrease the solubility of noscapine in the reaction mixture. In particular, the second solvent may have a low solubility for noscapine relative to the first solvent at a pH above about 5, as well as an essentially equivalent or higher solubility for any other impurities that are dissolved in the reaction mixture at a pH above about 5, including any impurities that undergo a color change when exposed to a pH greater than about 5, as described above. Further, the second solvent may be miscible with the first solvent in the reaction mixture.

(a) Composition of Second Solvent

The composition of the second solvent selected for use depends upon the composition of the first solvent in the reaction mixture. Any second solvent may be used, so long as the second solvent possesses the solubility and miscibility properties described above with respect to the first solvent.

Suitable second solvents for the method of the present invention include water, methanol, ethanol, isopropanol, pentanol, and combinations thereof. Preferred second solvents are water and ethanol. A particularly preferred second solvent is water.

(b) Quantity of Second Solvent

The quantity of second solvent that is contacted with the reaction mixture may be selected such that essentially the entire amount of noscapine contained in the opium source is recrystallized out of the reaction mixture. Therefore, the quantity of second solvent that is contacted with the reaction mixture is selected to reduce the solubility of the reaction mixture for noscapine to less than about 10% of the solubility of the reaction mixture prior to contact with the second solvent. The quantity of second solvent that is contacted with the reaction mixture may reduce the solubility of the reaction mixture for noscapine to less than about 9%, less than about 8%, less than about 7%, less than about 6%, less than about 5%, less than about 4%, less than about 3%, less than about 2%, less than about 1%, less than about 0.5%, or less than about 0.1% of the solubility of the reaction mixture for noscapine prior to contact with the second solvent.

The absolute quantity of second solvent that is suitable for the method of the present invention depends on the chemical properties of the specific first solvent and second solvent used, in particular the solubility of noscapine in the specific first solvent used. For example, if noscapine is highly soluble in the first solvent used in the reaction mixture, a greater quantity of second solvent may be necessary to reduce the solubility of the reaction mixture for noscapine to suitably low levels than if noscapine were somewhat less soluble in the first solvent.

The quantity of second solvent contacted with the reaction mixture source is selected to reduce the solubility of the reaction mixture for noscapine as described above. The amount of second solvent contacted with the reaction mixture may be from about 5% to about 500% of the volume of first solvent contacted with the noscapine to form the reaction mixture. The amount of second solvent contacted with the reaction mixture may be from about 5% to about 10%, about 9% to about 20%, about 19% to about 30%, about 29% to about 40%, about 39% to about 50%, about 49% to about 60%, about 59% to about 70%, about 69% to about 80%, about 79% to about 90%, about 89% to about 100%, about 99% to about 110%, about 109% to about 120%, about 119% to about 130%, about 129% to about 140%, about 139% to about 150%, about 149% to about 160%, about 159% to about 170%, about 169% to about 180%, about 179% to about 190%, about 189% to about 200%, about 199% to about 250%, about 249% to about 300%, about 299% to about 350%, about 349% to about 400%, about 399% to about 450%, and about 449% to about 500% of the volume of first solvent contacted with the noscapine to form the reaction mixture. Preferably, the amount of second solvent contacted with the reaction mixture is from about 40% to about 60% of the volume of first solvent contacted with the noscapine to form the reaction mixture.

(c) Other Properties of Second Solvent

The second solvent may have a pH ranging between about 4 and about 5, about 4.5 and about 5.5, about 5 and about 6, about 5.5 and about 6.5, about 6 and about 7, about 6.5 and about 7.5, about 7 and about 8, about 7.5 and about 8.5, 8 and about 9, about 8.5 and about 9.5, about 9 and about 10, about 9.5 and about 10.5, about 10 and about 11, and about 11.5 and about 12. The second solvent preferably has a pH of about 5 or above.

(V) Solvent Mixture

In an aspect of the present invention, a solvent mixture may be contacted with the opium source, resulting in a slurry that comprises the opium source and solvent mixture. The concentration of noscapine from the opium source in the solvent mixture is well above the solubility limit for noscapine in the solvent mixture, so that the noscapine remains essentially undissolved. In the slurry, the solvent mixture washes the opium source and dissolves away impurities, leaving behind purified noscapine. Solvent mixtures suitable for the method of the present invention may have a relatively low solubility for noscapine relative to the solubility of the solvent mixture for the impurities, including any impurities that undergo a color change when exposed to a pH greater than about 5, as described above.

(a) Composition of Solvent Mixture

The composition of the solvent mixture selected for use is a mixture of a first solvent selected from the group of first solvents described in Section (III) and a second solvent selected from the group of second solvents described in Section (IV). Any first and second solvents described above may be used for the solvent mixture, so long as the first and second solvent are miscible.

The concentration of the first solvent in the second solvent may range from about 10% to about 70% by weight. The concentration of the first solvent in the second solvent may range from about 10% to about 70%, about 10% to about 20%, about 15% to about 25%, about 20% to about 30%, about 25% to about 35%, about 30% to about 40%, about 35% to about 45%, about 40% to about 50%, about 45% to about 55%, about 50% to about 60%, about 55% to about 65%, and about 60% to about 70% by weight.

Suitable solvent mixtures include a mixture of acetonitrile and water at an acetonitrile concentration ranging between about 20% and about 70% by weight, and a mixture of acetone and water at an acetone concentration ranging between about 20% and about 60% by weight. A preferred solvent mixture is a mixture of acetonitrile and water at a concentration of about 50% by weight.

(b) Quantity of Solvent Mixture

The quantity of solvent mixture that is contacted with the opium source may be selected such that the concentration of noscapine from the opium source is well above the solubility limit of noscapine in the solvent mixture. Therefore, the quantity of solvent mixture that is contacted with the opium source is selected to result in a concentration of noscapine in the slurry that ranges between about 100% and about 30,000% of the solubility limit of noscapine in the solvent mixture. The quantity of solvent mixture that is contacted with the opium source is selected to result in a concentration of noscapine in the slurry that ranges between about 100% and about 200%, about 150% and about 250%, about 200% and about 300%, about 250% and about 350%, about 300% and about 400%, about 350% and about 450%, about 400% and about 500%, about 450% and about 550%, about 500% and about 600%, about 550% and about 650%, about 600% and about 700%, about 650% and about 750%, about 700% and about 800%, about 750% and about 850%, about 800% and about 900%, about 850% and about 950%, about 900% and about 1,000%, about 950% and about 1,050%, about 1,000% and about 2,000%, about 1,500% and about 2,500%, about 2,000% and about 3,000%, about 2,500% and about 3,500%, about 3,000% and about 4,000%, about 3,500% and about 4,500%, about 4,000% and about 5,000%, about 4,500% and about 5,500%, about 5,000% and about 10,000%, about 7,500% and about 12,500%, about 10,000% and about 15,000%, about 12,500% and about 17,500%, about 15,000% and about 20,000%, about 17,500% and about 22,500%, about 20,000% and about 25,000%, about 22,500% and about 27,500%, and about 25,000% and about 30,000% of the solubility limit of noscapine in the solvent mixture. A preferred quantity of solvent mixture that is contacted with the opium source is selected to result in a concentration of noscapine in the slurry that ranges between about 500% and about 1500% of the solubility limit of noscapine in the solvent mixture.

The absolute quantity of second solvent that is suitable for the method of the present invention depends on the chemical properties of the specific first solvent and second solvent used, in particular the solubility of noscapine in the specific first solvent used. For example, if the solvent mixture has a relatively high concentration of first solvent relative to concentration of second solvent by weight, less solvent mixture may be used than if the solvent mixture contains a relatively low concentration of first solvent.

(c) Temperature of Solvent Mixture

The temperature of the solvent mixture that is contacted with the opium source may be selected such that the solubility of noscapine in the solvent mixture is minimal relative to the solubility of the impurities in the solvent mixture. The temperature of the solvent mixture may range between the eutectic temperature of the solvent mixture and the lower boiling point temperature of the first solvent and the second solvent included in the solvent mixture. The temperature of the solvent mixture may range from about 0° C. to about 100° C., from about 0° C. to about 10° C., from about 9° C. to about 20° C., from about 19° C. to about 30° C., from about 29° C. to about 40° C., from about 39° C. to about 50° C., from about 49° C. to about 60° C., from about 59° C. to about 70° C., from about 69° C. to about 80° C., from about 79° C. to about 90° C., and from about 89° C. to about 100° C. The temperature may be maintained at an essentially constant value throughout all steps of the method, or the temperature may be allowed to vary during the steps of the method.

(d) Other Properties of Solvent Mixture

The solvent mixture may have a pH ranging between about 4 and about 5, about 4.5 and about 5.5, about 5 and about 6, about 5.5 and about 6.5, about 6 and about 7, about 6.5 and about 7.5, about 7 and about 8, about 7.5 and about 8.5, about 8 and about 9, about 8.5 and about 9.5, about 9 and about 10, about 9.5 and about 10.5, about 10 and about 11, about 11.5 and about 12. The second solvent preferably has a pH of about 5 or above.

(VI) Process Conditions for Noscapine Removal Method

The process conditions for the method of the present invention are selected to maximize the amount of noscapine purified from the opium source, and to minimize the impurities in the noscapine produced by the method, and to avoid the formation of impurities that may impart undesirable color characteristics to the noscapine produced by the method. In particular, the pH and the temperature at which the method of the present invention is conducted affect the yield and purity of the noscapine purified using the method of the present invention.

(a) pH

The pH at which the method of the present invention is conducted is generally greater than about 5. The pH at which the method of the present invention is conducted may range between about 5 and about 6, about 5.5 and about 6.5, about 6 and about 7, about 6.5 and about 7.5, 7 and about 8, about 7.5 and about 8.5, about 8 and about 9, about 8.5 and about 9.5, about 9 and about 10, about 9.5 and about 10.5, about 10 and about 11, and about 11.5 and about 12. The pH may be maintained at an essentially constant value throughout all steps of the method, the pH may be allowed to vary during the steps of the method, or the pH may be maintained at a different value for one step and at a second value for another step of the method. For example, the first solvent may be contacted with the opium source at a pH of about 5, and the second solvent may be contacted with the reaction mixture at a pH of about 11.

(b) Temperature

The temperature at which the method of the present invention is conducted may be selected to enhance the solubility characteristics of noscapine in the first solvent when the first solvent is contacted with the opium source, and to reduce further the solubility of noscapine in the reaction mixture after the reaction mixture is contacted with the second solvent. Therefore, the temperature at which the method of the present invention is conducted depends upon the composition of the first and second solvents used. Without being bound to any particular theory, the solubility of a compound in a solvent generally increases at higher solvent temperatures and decreases at lower solvent temperatures.

The temperature at which the method of the present invention is conducted may range between the eutectic temperature of the reaction mixture after the second solvent is added, and the boiling point of the first solvent. This temperature range prevents the reaction mixture from boiling off when the first solvent is initially contacted with the opium source, and further avoids solidifying the reaction mixture after being contacted with the second solvent. The temperature at which the method of the present invention is conducted may range from about 0° C. to about 100° C., from about 0° C. to about 10° C., from about 9° C. to about 20° C., from about 19° C. to about 30° C., from about 29° C. to about 40° C., from about 39° C. to about 50° C., from about 49° C. to about 60° C., from about 59° C. to about 70° C., from about 69° C. to about 80° C., from about 79° C. to about 90° C., and from about 89° C. to about 100° C. The temperature may be maintained at an essentially constant value throughout all steps of the method, the temperature may be allowed to vary during the steps of the method, or the temperature may be maintained at a different value for one step and at a second value for another step. For example, the first solvent may be contacted with the opium source at a temperature of about 50° C., and the reaction mixture may be cooled to a temperature of about 22° C. after the reaction mixture is contacted with the second solvent.

In an embodiment, the temperature at which the method of the present invention is conducted may range between the eutectic temperature of the solvent mixture, and the boiling point of the solvent mixture. Temperatures at which the solvent mixture is contacted with the opium source to form a slurry range from about 20° C. to about 760° C., from about 20° C. to about 24° C., from about 23° C. to about 25° C., from about 24° C. to about 26° C., from about 25° C. to about 27° C., from about 26° C. to about 28° C., from about 27° C. to about 29° C., from about 28° C. to about 30° C., from about 25° C. to about 35° C., from about 30° C. to about 40° C., from about 35° C. to about 45° C., from about 40° C. to about 50° C., from about 45° C. to about 55° C., from about 50° C. to about 60° C., from about 55° C. to about 65° C., and from about 65° C. to about 70° C. A preferred temperature at which the solvent mixture is contacted with the opium source to form a slurry ranges from about 20° C. to about 25° C.

(VII) Other Aspects of Method

The method of the present invention may further comprise additional steps to enhance the yield, purity, and color characteristics of noscapine product resulting from the method. Additional steps may include filtration of the noscapine crystals and rinsing of the filtered noscapine crystals with a rinse solvent.

(a) Filtration

After recrystallizing the noscapine by contacting the second solvent with the reaction mixture, the resulting noscapine crystals may be filtered from the reaction mixture solvents using known filtration methods. Suitable filtration media may include filtration through filter paper used with a Buchner funnel, Hirsch funnel, or other filter funnel, and filtration though a sintered-glass funnel. Suitable filtration methods may include gravity filtration, pressure filtration, side stream filtration, depth filtration, continuous rotary filtration and centrifugation.

(b) Rinsing of Filtered Noscapine Crystals

The method of the present invention may further comprise rinsing the filtered noscapine crystals with a rinse solvent. Without being bound to any particular theory, rinsing may wash away residual impurities that may have adhered to the noscapine crystals during the filtration process. Thus, rinsing the noscapine crystals may enhance the purity of the noscapine resulting from the method of the present invention. However, if the rinse solvent also rinses away some fraction of the crystallized noscapine in addition to the impurities, then rinsing the noscapine crystals may decrease the overall yield of purified noscapine. Two factors that contribute to the effectiveness of the rinsing process are the composition of the rinse solvent and the amount of rinse solvent used to rinse the filtered noscapine crystals.

(i) Composition of Rinse Solvent

The rinse solvent used to rinse the filtered noscapine crystals is selected to possess a high solubility for the impurities described above, including the impurities that undergo a color change when exposed to a pH less than about 5. The rinse solvent may be mixtures of water and a second rinse solvent, including methanol, ethanol, isopropanol, pentanol, acetonitrile, acetone, and combinations thereof.

The concentration of the second rinse solvent in the rinse solvent may range from 0% to about 70% by weight. The concentration of the solvent in the rinse solvent may range from 0% to about 5%, about 3% to about 8%, about 5% to about 10%, about 8% to about 13%, about 10% to about 15%, 12% to about 17%, 15% to about 20%, 17% to about 22%, 20% to about 25%, 22% to about 27%, 25% to about 30%, 27% to about 32%, 30% to about 35%, 32% to about 37%, 35% to about 40%, 37% to about 42%, 40% to about 45%, 42% to about 47%, 45% to about 50%, 47% to about 52%, 50% to about 55%, 52% to about 57%, 55% to about 60%, 62% to about 67%, and 65% to about 70% by weight. Exemplary rinse solvents include 33% by weight solution of isopropanol in water, 20% by weight solution of acetonitrile in water, and 100% water.

(i) Amount of Rinse Solvent

The amount of rinse solvent used to rinse the filtered noscapine crystals is selected such that any residual impurities adhered to the filtered noscapine crystals are essentially rinsed off of the crystals, while avoiding significant loss of noscapine. The amount of rinse solvent used in the rinsing of the filtered noscapine crystals depends on the composition of the rinse solvent. For example, rinse solvents with a relatively high concentration of second rinse solvent may achieve similar results with a lower amount of rinse solvent than rinsing with a lower concentration of second rinse solvent.

The amount of rinse solvent used to rinse the filtered noscapine crystals may range from about 1 g to about 50 g of rinse solvent per gram of noscapine crystals. The amount of rinse solvent may range from about 1 g to about 5 g, from about 3 g to about 7 g, from about 5 g to about 10 g, from about 7 g to about 13 g, from about 10 g to about 15 g, from about 17 g to about 23 g, from about 20 g to about 25 g, from about 27 g to about 33 g, from about 25 g to about 30 g, from about 27 g to about 33 g, from about 30 g to about 35 g, from about 32 g to about 37 g, from about 35 g to about 40 g, from about 37 g to about 43 g, from about 40 g to about 45 g, from about 43 g to about 47 g, and from about 45 g to about 50 g of rinse solvent per gram of filtered noscapine crystals. Preferably, the amount of rinse solvent may range from about 5 g to about 25 g of rinse solvent per gram of filtered noscapine crystals.

(VIII) Purified Noscapine Product

The quality of the noscapine product produced by the method of the present invention may be assessed using the color of the noscapine crystals, the purity of the noscapine product, and the yield of the noscapine product, described below.

(a) Color of Noscapine Product

The method of the present invention described above provides a method of removing impurities that undergo an irreversible color change when exposed to a pH of about 5. The purified noscapine product that results from the method of the present invention may range from a light tan color to a white color. Preferably, the noscapine product that results from the method of the present invention has a white color.

(b) Purity Of Noscapine Product

The purity of the noscapine product resulting from the method of the present invention is defined as the proportion of the noscapine product that comprises noscapine, expressed as a percentage of the total weight of the noscapine product. In general, purity is a quantity that expresses the effectiveness of the method of the present invention at removing impurities from the opium source. The more impurities that are removed by the method of the present invention, the higher the purity of the resulting noscapine product.

The purity of the noscapine product that results from the method of the present invention may range from about 20% to 100% by weight. The purity of the noscapine product that results from the method of the present invention may range from 100% to about 98%, about 99% to about 97%, about 98% to about 96%, about 97% to about 95%, about 96% to about 94%, about 95% to about 93%, about 94% to about 92%, about 93% to about 91%, about 92% to about 90%, about 91% to about 89%, about 90% to about 88%, about 89% to about 87%, about 88% to about 86%, about 87% to about 85%, about 86% to about 84%, about 85% to about 83%, about 84% to about 82%, about 83% to about 81%, about 82% to about 80%, about 81% to about 79%, about 80% to about 75%, about 76% to about 70%, about 71% to about 65%, about 66% to about 60%, about 61% to about 55%, about 56% to about 50%, about 51% to about 45%, about 46% to about 40%, about 41% to about 35%, about 36% to about 30%, about 31% to about 25%, and about 26% to about 20% by weight. Preferably, the noscapine product that results from the method of the present invention has a purity of at least 98% by weight.

(a) Yield of Noscapine Product

The yield of the noscapine product resulting from the method of the present invention is defined as the amount of the noscapine product that comprises noscapine, expressed as a percentage of noscapine contained in the opium source used as feedstock to the method of the present invention. In general, yield is a quantity that expresses the efficiency of the method of the present invention at removing impurities from the opium source while minimizing the loss of noscapine during processing. A high noscapine yield indicates that minimal noscapine was removed from the opium source using the method of the present invention.

The yield of the noscapine product that results from the method of the present invention may range from 100% to about 20% of the weight of noscapine in the opium source. The yield of the noscapine product that results from the method of the present invention may range from 100% to about 98%, about 99% to about 97%, 98% to about 96%, 97% to about 95%, 96% to about 94%, 95% to about 93%, 94% to about 92%, 93% to about 91%, 92% to about 90%, 91% to about 89%, 90% to about 88%, 89% to about 87%, 88% to about 86%, 87% to about 85%, 86% to about 84%, 85% to about 83%, 84% to about 82%, 83% to about 81%, 82% to about 80%, 81% to about 79%, 80% to about 75%, 76% to about 70%, 71% to about 65%, 66% to about 60%, 61% to about 55%, 56% to about 50%, 51% to about 45%, 46% to about 40%, 41% to about 35%, 36% to about 30%, 31% to about 25%, and 26% to about 20% of the weight of noscapine in the opium source. Preferably, the noscapine product that results from the method of the present invention has a purity of at least 80% of the weight of noscapine in the opium source.

(IX) Exemplary Embodiments of the Method

In an exemplary embodiment, the method of the present invention comprises contacting the opium source described in section (II) with a first solvent described in section (III) to form a reaction mixture. The method further comprises contacting the reaction mixture with a second solvent described in section (IV), thereby recrystallizing the noscapine out of the reaction mixture. The method may further comprise filtering the noscapine crystals, as described in section (VII)(a). The method may further comprise rinsing the filtered crystals with a rinse solvent as described in section (VII)(b).

In an exemplary embodiment, the method of the present invention comprises contacting the opium source described in section (II) with a solvent mixture described in section (V) to form a slurry. The method may further comprise filtering the noscapine crystals from the slurry, as described in section (VII)(a). The method may further comprise rinsing the filtered crystals with a rinse solvent as described in section (VII)(b).

In an embodiment, the opium source described in section (II) is contacted with acetonitrile at a temperature of about 70° C. to a concentration of about 200 mg of noscapine per gram of acetonitrile to form a reaction mixture comprising a pH greater than about 5. The reaction mixture is then slowly cooled to a temperature ranging between about 20° C. and 30° C. The noscapine may then be recrystallized by contacting the reaction mixture with an amount of water roughly equal to the amount of acetonitrile in the reaction mixture. The resulting noscapine crystals may then be filtered and rinsed with a 20% acetonitrile solution by weight in water, followed by a second rinse in water.

In an embodiment, the opium source described in section (II) is contacted with acetone at a temperature of about 50° C. to a concentration ranging between about 100 and about 120 mg of noscapine per gram of acetone to form a reaction mixture. The reaction mixture is then slowly cooled to a temperature ranging between about 20° C. and 30° C. The noscapine was then recrystallized by contacting the reaction mixture with an amount of water roughly equal to the amount of acetone in the reaction mixture. The resulting white noscapine crystals are then filtered and rinsed with a 20% acetonitrile solution by weight in water, followed by a second rinse in water.

In an embodiment, the opium source is contacted with a mixture of about 40% and about 60% acetonitrile by weight in water to form a slurry with about 2 g to about 30 g of solvent mixture per gram of noscapine at a temperature ranging between about 20° C. and 70° C. The resulting noscapine crystals may then be filtered and rinsed with a 20% acetonitrile solution by weight in water, followed by a second rinse in water.

Other exemplary iterations of the method are described herein and in the examples.

Definitions

As used herein, the term "yield" refers to the amount of purified noscapine resulting from the method of the present invention, expressed as a percentage of the noscapine contained in the opium source.

The term "purity" as used herein, refers to the proportion of the final product resulting from the method of the present invention that comprises noscapine, expressed as percent of the total final product by weight.

The term "poppy straw" as used herein, refers to a mixture of stems and capsules from the harvested opium poppy, *Papaver somniferum*.

As various changes could be made in the above methods without departing from the scope of the invention, it is intended that all matter contained in the above description and in the examples given below, shall be interpreted as illustrative and not in a limiting sense.

EXAMPLES

The following examples illustrate various embodiments of the invention.

Example 1

Determination of Noscapine pKa

Figure 5:
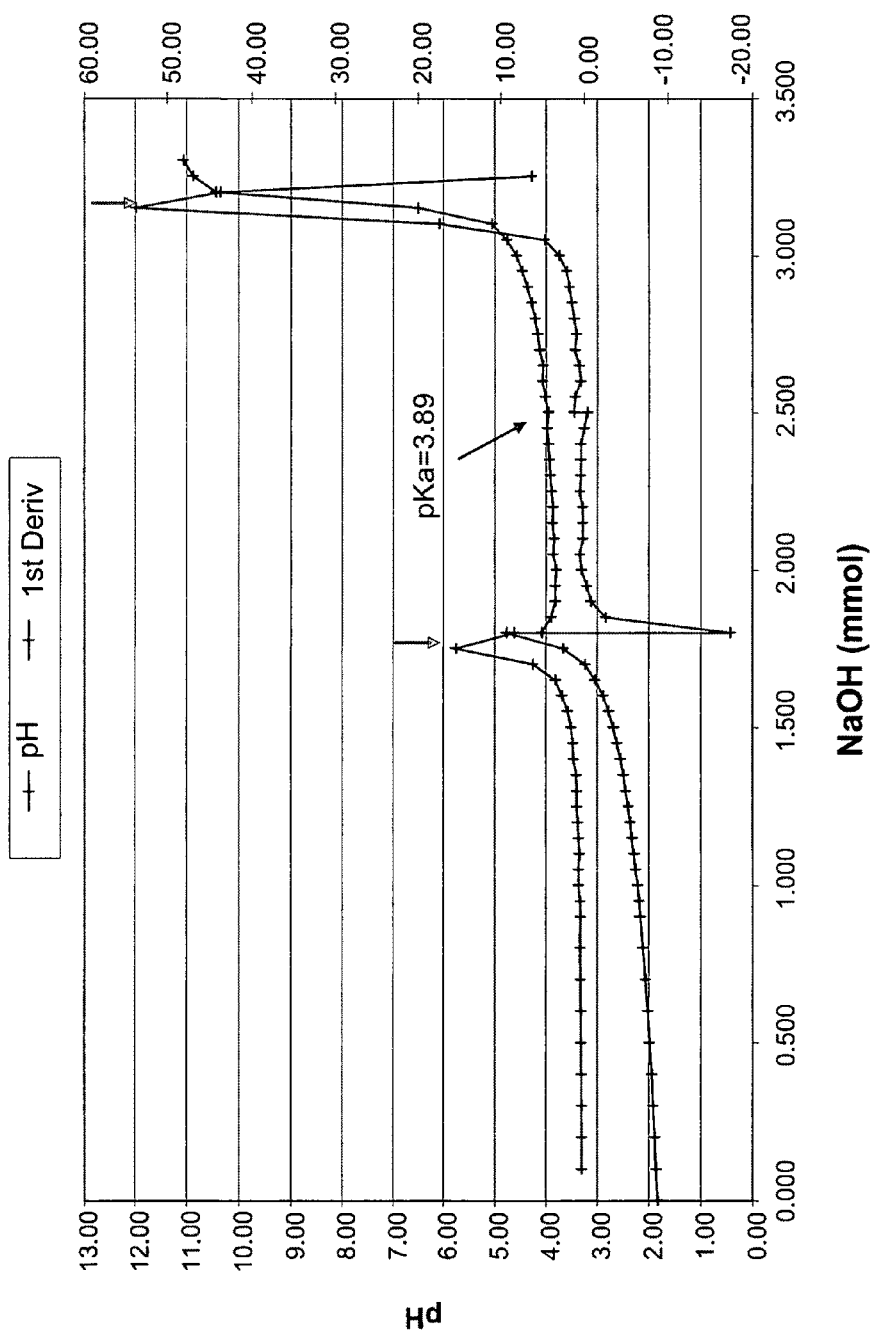
FIG. 5 is a titration curve for noscapine.

To determine the pH at which noscapine and various impurities precipitate after dissolution in an acid solution, the following experiments were conducted. Pure noscapine was added to water, and a 37% solution of hydrochloric acid by weight was added to the mixture to lower the pH of the mixture to about 2. A titration curve was obtained by gradually adding 0.1 N sodium hydroxide solution while monitoring the pH of the mixture. A titration curve summarizing the results of this experiment is shown in FIG. 5.

Figure 6:
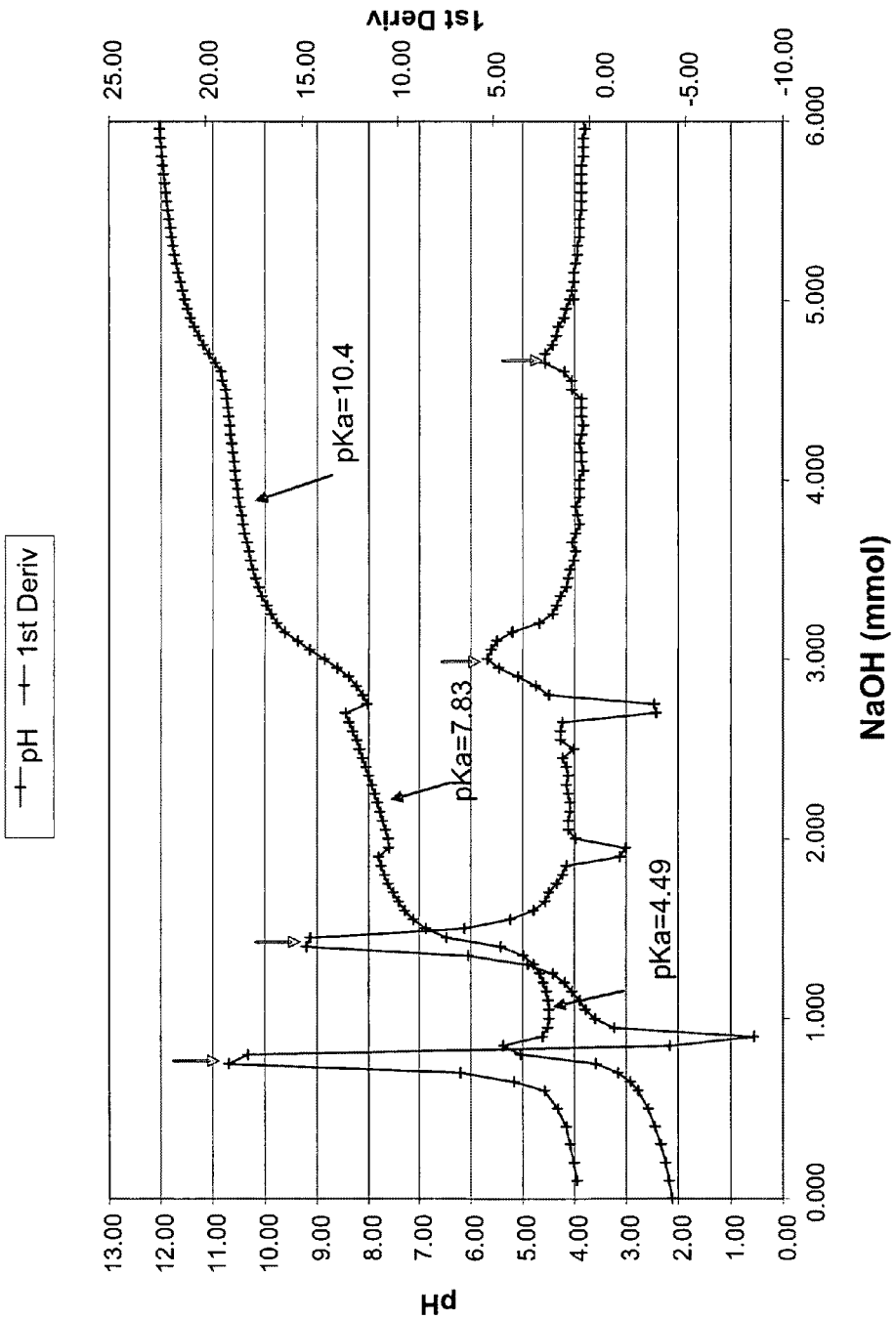
FIG. 6 is a titration curve for a mixture of noscapine, morphine, and oripavine.

In a second experiment, equal parts of noscapine, morphine and oripavine were mixed with water and the pH of the mixture was raised to about 2 by the addition of hydrochloric acid as before. A titration curve was obtained by adding sodium hydroxide while measuring the pH of the mixture as before. FIG. 6 shows a titration curve summarizing the results of this experiment.

Figure 7:
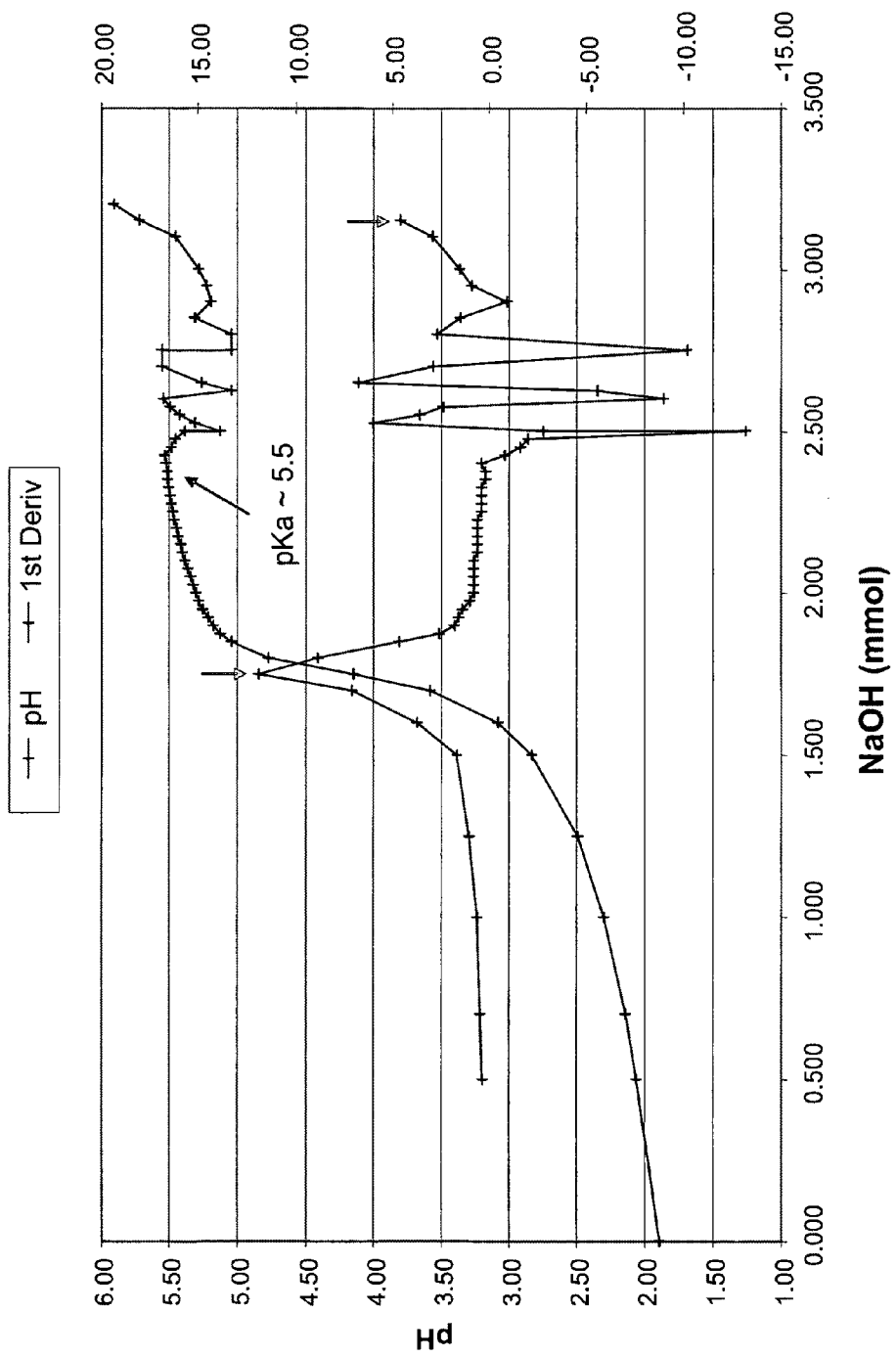
FIG. 7 is a titration curve for a mixture of noscapine and concentrated poppy straw.

A third experiment mixed noscapine with concentrated poppy straw containing morphine (84.01% by weight), oripavine (4.39% by weight), codeine (0.15% by weight), and thebaine (0.59% by weight) in water. Hydrochloric acid was added to adjust the pH of the solution to about 2, and a titration curve was obtained by gradually adding sodium hydroxide solution while measuring the pH of the mixture as before. The resulting titration curve is shown in FIG. 7.

The results of this experiment indicated that noscapine may be separated from other impurities by dissolving the noscapine-containing material in a acidic solution, and then raising the pH of the mixture slightly. The titration curve shown in FIG. 6 indicated that noscapine precipitates out of the acidic solution at a pH of 4.5 to 5.5, and morphine and oripavine precipitate out of solution together at a pH of 7.0 to 8.5. FIG. 5 and FIG. 7 further indicated that the pH at which noscapine precipitates out of solution was not sensitive to the presence of other dissolved contaminants in the mixture.

Example 2

Analysis of CPS Impurities

To determine the composition of the red-colored and pink-colored impurities observed in noscapine products resulting from acidic process conditions, the following experiment was conducted. Initially, a portion of yellow-colored noscapine that was extracted at a pH of 13 was acid-treated at a pH of 1.3 and heated to 45-55° C. The extract gradually turned red over a 30-minute period.

Concentrated poppy straw (CPS) was obtained that contained 52.5% noscapine, 13.3% thebaine, 2.0% papaverine, 0.062% codeine, and 0.391% cryptopine by weight. The CPS was a tan-colored free-flowing dry powder.

Noscapine was extracted from the CPS, and the extracts were treated with strong acid to a pH of 2 and heated to 50° C. for 30 minutes to form red iminium salt solutions. Samples of each extract (both before and after acid treatment) were subjected to UV scanning to determine the ideal wavelength(s) for identifying the red-colored bodies. UV scans of both solutions showed peak wavelengths at 280-285 nm.

Dual-wavelength runs were performed using a Waters HPLC to characterize the papaverrubines and the red iminium salts on the chromatographs. Examination of the chromatographs revealed nine unknown impurity peaks. At least eight of the chromatographic peaks as determined by UV scanning could potentially be papaverrubines, and at least four of the chromatographic peaks could potentially be red iminium salts.

The results of this experiment identified at least eight potential papaverrubine contaminants in the CPS from which noscapine was purified. The results of this experiment further determined that the red-colored bodies formed in many of the extraction methods were most likely iminium salts formed from one or more papaverrubine contaminants when exposed to acidic (i.e., a pH less than about 2) conditions. A noscapine purification method in which all steps occurred at a pH well above 2 may prevent the formation of the red iminium salt contaminants.

Example 3

Survey of Noscapine Solubility in Selected Solvents at Neutral pH

To determine the solubility of noscapine in a variety of different solvents at neutral pH, the following experiment was conducted. Noscapine solubility was determined at ambient temperature (22° C.-23° C.) and at 50° C. by dissolving noscapine and noting the amount dissolved prior to saturation for the following solvents: acetone, acetonitrile, ethanol, isopropanol, methanol, pentanol, toluene, and water. The solubilities measured in this experiment are summarized in Table 1.

TABLE 1

Solubilities of noscapine in pure solvents.

| Solvent | Solubility (mg of noscapine/g of solvent) | |
|---|---|---|
| | 23° C. | 50° C. |
| Acetone | 68.56 | 145.98 |
| Acetonitrile | 52.33 | 151.21 |
| Chloroform | 504.11 | |
| Toluene | 40.65 | 59.99 |
| Water | | 0.82 |
| Methanol | | 1.81 |
| Ethanol | | 5.90 |
| Isopropanol | | 12.99 |
| Pentanol | | 12.29 |

Noscapine possesses a wide spectrum of solubilities in various solvents, ranging from highly soluble in chloroform to nearly insoluble in water. Further, the solubilities of noscapine in acetone and acetonitrile were relatively sensitive to increases in temperature from 23° C. to 50° C., whereas the solubility of noscapine in toluene was relatively less sensitive to equivalent changes in solvent temperature.

Noscapine solubility was also determined at room temperature for the following solvent mixtures, mixed in a roughly 1:1 ratio by weight: acetone:water, acetonitrile:water, chloroform:ethanol, toluene:ethanol. Solubilities were determined using methods similar to those described above, and the measured solubilities are summarized in Table 2.

TABLE 2

Solubilities of noscapine in solvent mixtures.

| Solvent 1 | | Solvent 2 | | |
|---|---|---|---|---|
| Solvent name | % weight | Solvent name | % weight | Solubility (mg noscapine/g of solvent) |
| Acetone | 49.4% | Water | 50.6% | 3.21 |
| Acetonitrile | 48.6% | Water | 51.4% | 1.06 |
| Chloroform | 50.0% | Ethanol | 50.0% | 73.34 |
| Toluene | 51.0% | Ethanol | 49.0% | 37.21 |

The solubilities of noscapine in the four solvents in which noscapine was most highly soluble were uniformly reduced by the addition of one of the two solvents in which noscapine was least soluble. Comparing Table 1 and Table 2, adding an equal amount of water to acetone and water reduced the solubility of noscapine in the solvents by about 95% and about 98%, respectively.

The results of this experiment characterized the solubility of noscapine in a variety of pure solvents and solvent mixtures. The wide range of solubilities in different solvents and mixtures may be exploited to develop extraction techniques in which the crude noscapine is dissolved in one of the solvents such as acetone or acetonitrile, and then recrystallized by the addition of one of other solvents such as water.

Example 4

Purification of Concentrated Poppy Straw Using Dissolution in Acetonitrile Followed by Crystallization with Water To determine the effectiveness of a method of acetonitrile dissolution/water crystallization method at removing impurities from a crude noscapine source, the following experiment was conducted. Concentrated poppy straw (CPS) similar to that described in Example 2 was obtained. The CPS was dissolved in pure acetonitrile at a temperature of 50° C. and to a concentration of 136 mg of noscapine per gram of acetonitrile. Filter aids were added to the mixture, and the mixture was then filtered. After cooling the filtrate to room temperature, an amount of water roughly equal to the amount of acetonitrile was added to the mixture to recrystallize the noscapine. Noscapine crystals formed and collected at the bottom of the vial. The precipitates were tan in color, and the mother liquor was dark brown.

The results of this experiment demonstrated that acetonitrile extraction followed by water recrystallization appeared to be a viable noscapine purification method for the CPS used in this experiment.

Example 5

Purification of Concentrated Poppy Straw Using Dissolution in Acetone Followed by Crystallization with Water To determine the effectiveness of a method of acetone dissolution/water crystallization method at removing impurities from a crude noscapine source, the following experiment was conducted. Concentrated poppy straw (CPS) similar to that described in Example 2 was obtained. The CPS was dissolved in pure acetone at a temperature of 50° C. and to a concentration of 132 mg of noscapine per gram of acetone. Filter aids were added to the mixture, and the mixture was then filtered. After cooling the filtrate to room temperature, an amount of water roughly equal to the amount of acetone was added to the mixture to recrystallize the noscapine. Noscapine crystals formed and collected at the bottom of the vial. The precipitates were tan in color, and the mother liquor was dark brown.

In addition, a larger batch of CPS was treated using the same method. CPS was dissolved in acetonitrile at 50° C. at an approximate concentration of 150 mg of noscapine per gram of acetonitrile. A quantity of water roughly equal in mass to the amount of acetonitrile was slowly added to the mixture, while maintaining the mixture at 50° C. The mixture was allowed to gradually cool to room temperature, and then the mixture was placed in an ice bath. The resulting noscapine crystals were light tan in color, with a yield of 86% of the original noscapine in the CPS, and a purity of 92%.

The results of this experiment demonstrated that acetone extraction followed by water recrystallization appeared to be a viable noscapine purification method for the CPS used in this experiment.

Example 6

Purification of Concentrated Poppy Straw Using Dissolution in Acetone Followed by Crystallization with Water To determine the effectiveness of a method of acetone dissolution/water crystallization method at removing impurities from a crude noscapine source, the following experiment was conducted. Concentrated poppy straw (CPS) similar to that described in Example 2 was obtained. The CPS was dissolved in pure acetone at a temperature of 50° C. and to a concentration of 132 mg of noscapine per gram of acetone. Filter aids were added to the mixture, and the mixture was then filtered. After cooling the filtrate to room temperature, an amount of water roughly equal to the amount of acetone was added to the mixture to recrystallize the noscapine. Noscapine crystals formed and collected at the bottom of the vial. The precipitates were tan in color, and the mother liquor was dark brown.

The results of this experiment demonstrated that acetone extraction followed by water recrystallization appeared to be a viable noscapine purification method for the CPS used in this experiment.

Example 7

Figure 8:
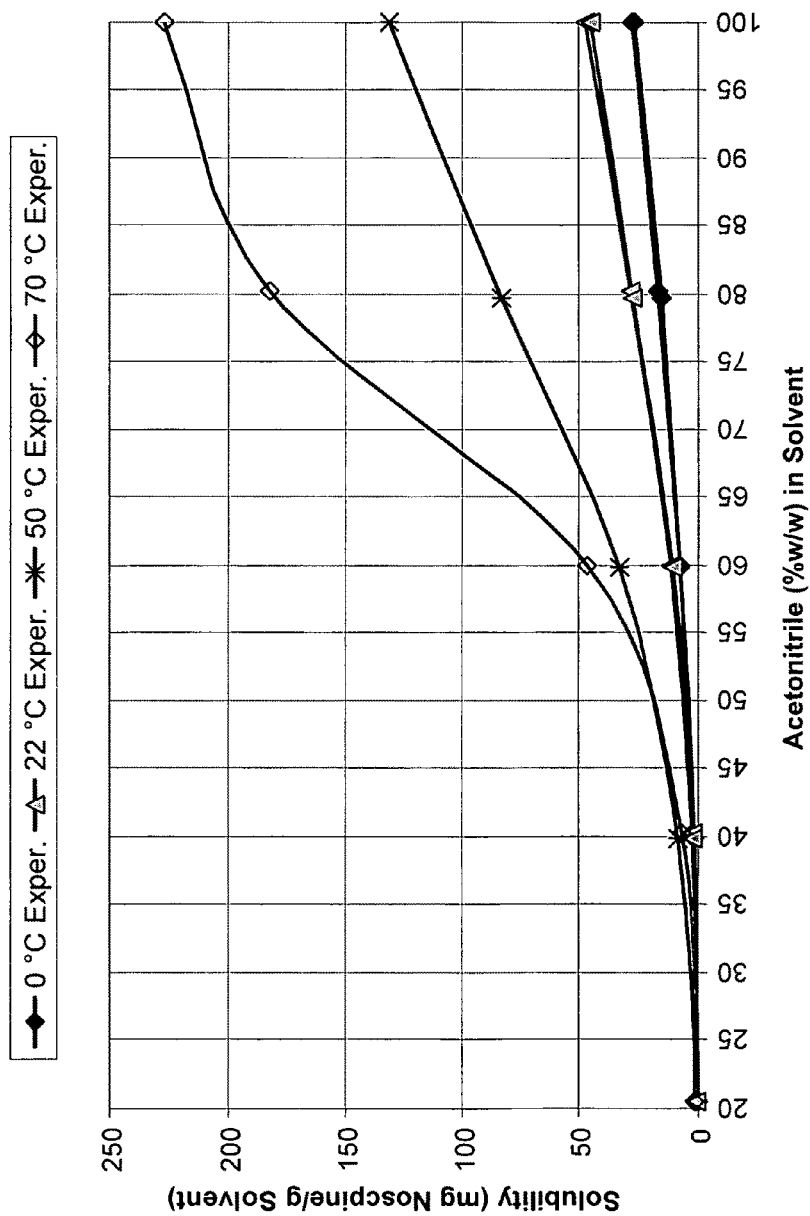
FIG. 8 is a summary of the solubility of noscapine in acetonitrile/water mixtures.

Sensitivity of the Solubility of Noscapine in a Acetonitrile/Water System to Variations in Temperature and Acetonitrile Concentration To characterize the solubility of noscapine in acetonitrile/water systems, the following experiment was conducted. Noscapine solubility was determined at 0° C., 22° C., 50° C., and 70° C. in mixtures of acetonitrile and water in which the acetonitrile concentrations were 0%, 20%, 40%, 60%, 80%, and 100% by weight. The results of the solubility measurements are summarized in Table 3 and are summarized in a graph in FIG. 8.

TABLE 3

Solubility of noscapine in acetonitrile and water.

| Proportion of acetonitrile by weight | Solubility (mg noscapine per gram of solvent) measured at solvent temperature of: | | | |
|---|---|---|---|---|
| | 0° C. | 22° C. | 50° C. | 70° C. |
| 0% | 0.1 to 0.6 | 0.1 to 0.2 | 0.2 | 0.2 |
| 20% | 0.2 to 0.6 | 0.6 to 0.9 | 0.8 | 1.4 |
| 40% | 1.9 to 2.0 | 2.6 to 2.6 | 8.1 | 6.7 |
| 60% | 7.9 to 8.0 | 10.9 to 11.3 | 32.6 | 46.3 |
| 80% | 15.6 to 16.7 | 27.6 to 28.0 | 82.8 | 181.9 |
| 100% | 26.9 to 27.7 | 44.8 to 47.3 | 131.0 | 226.5 |

Noscapine solubility was highly sensitive to changes in solvent temperature and acetonitrile concentration. The solubility of noscapine in the acetonitrile/water mixture increased by up to 10-fold between 0° C. and 70° C. at acetonitrile concentrations of about 50% or above. Further, the sensitivity of the solubility of noscapine in the acetonitrile/water solvent was much greater at the higher temperatures. The ratio of the solubility of noscapine in pure acetonitrile to the solubility of noscapine in pure water was about 78 at a solvent temperature of 0° C.; this same ratio increased to a value of about 647 at a solvent temperature of 70° C.

The results of this experiment demonstrated that the solubility of noscapine in an acetonitrile/water solvent was sensitive to both temperature and acetonitrile concentration, for acetonitrile concentrations above about 40% by weight.

Example 8

Figure 9:
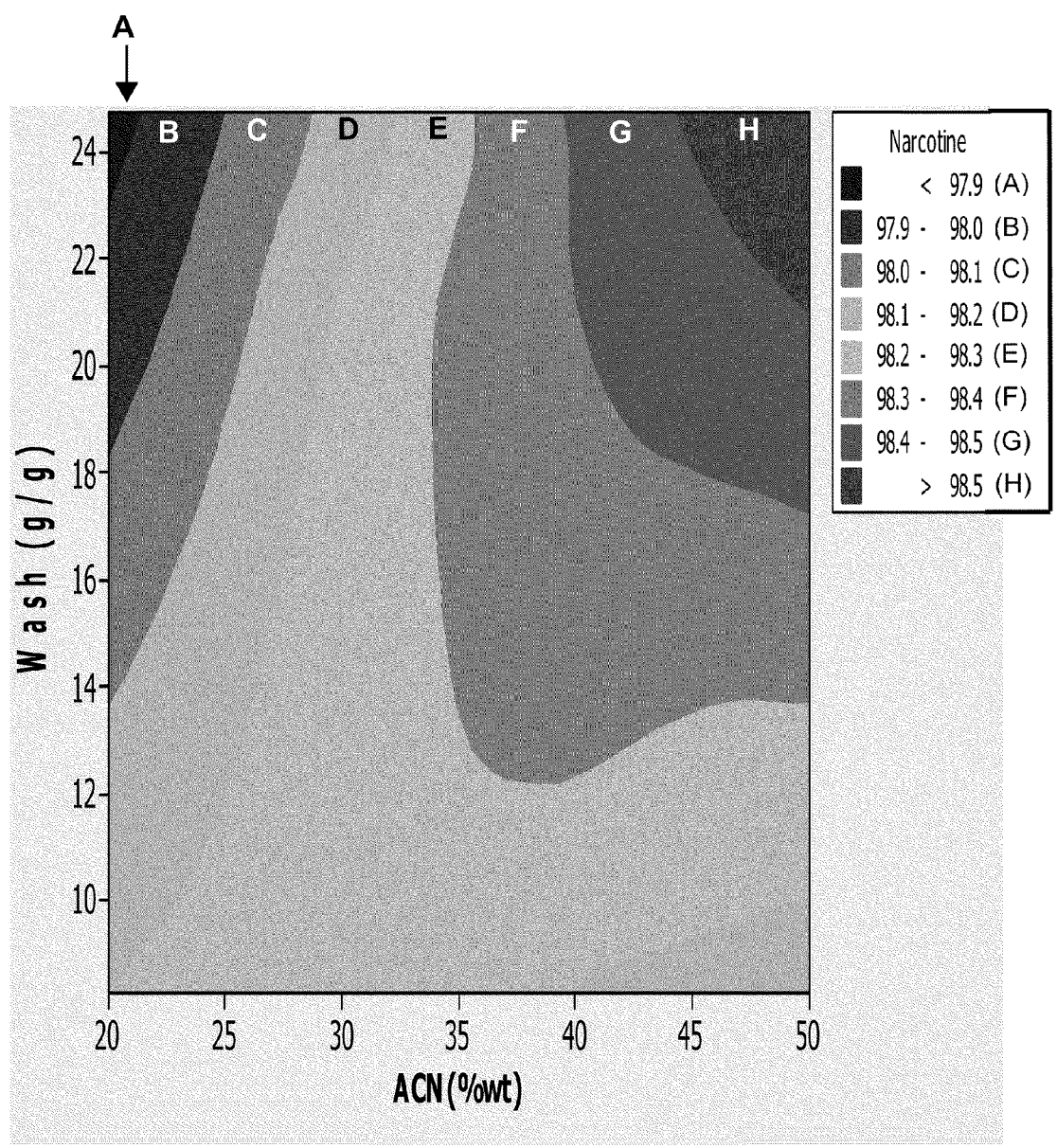
FIG. 9 is a contour plot summarizing the effects of wash ratio and acetonitrile wash solvent concentration on the purity of the resulting noscapine product.

Impact of Acetonitrile Concentration and Wash Volume on the Purification of Noscapine To assess the impact of varying acetonitrile concentration and wash volume on the purification of noscapine from CPS, the following experiment was conducted. High-noscapine concentrated poppy straw (CPS) containing 97.94% noscapine, 0.34% papaverine, 0.03% crypotopine, and 0.38% thebaine was obtained. Samples of the high-noscapine CPS were slurry-washed with acetonitrile/$H_2O$ solutions in which the acetonitrile concentrations ranged from 20% to 50% by weight. The wash ratios varied from 8.25 grams to 24.75 of wash solvent per gram of noscapine. The purity of the noscapine after the slurry-wash is summarized in FIG. 9 for all conditions tested. The yield of noscapine as a percent of the original noscapine content prior to the slurry-washing is summarized in FIG. 10. The concentration of narcotoline impurity as a percent mass of the noscapine product summarized in FIG. 11.

Figure 10:
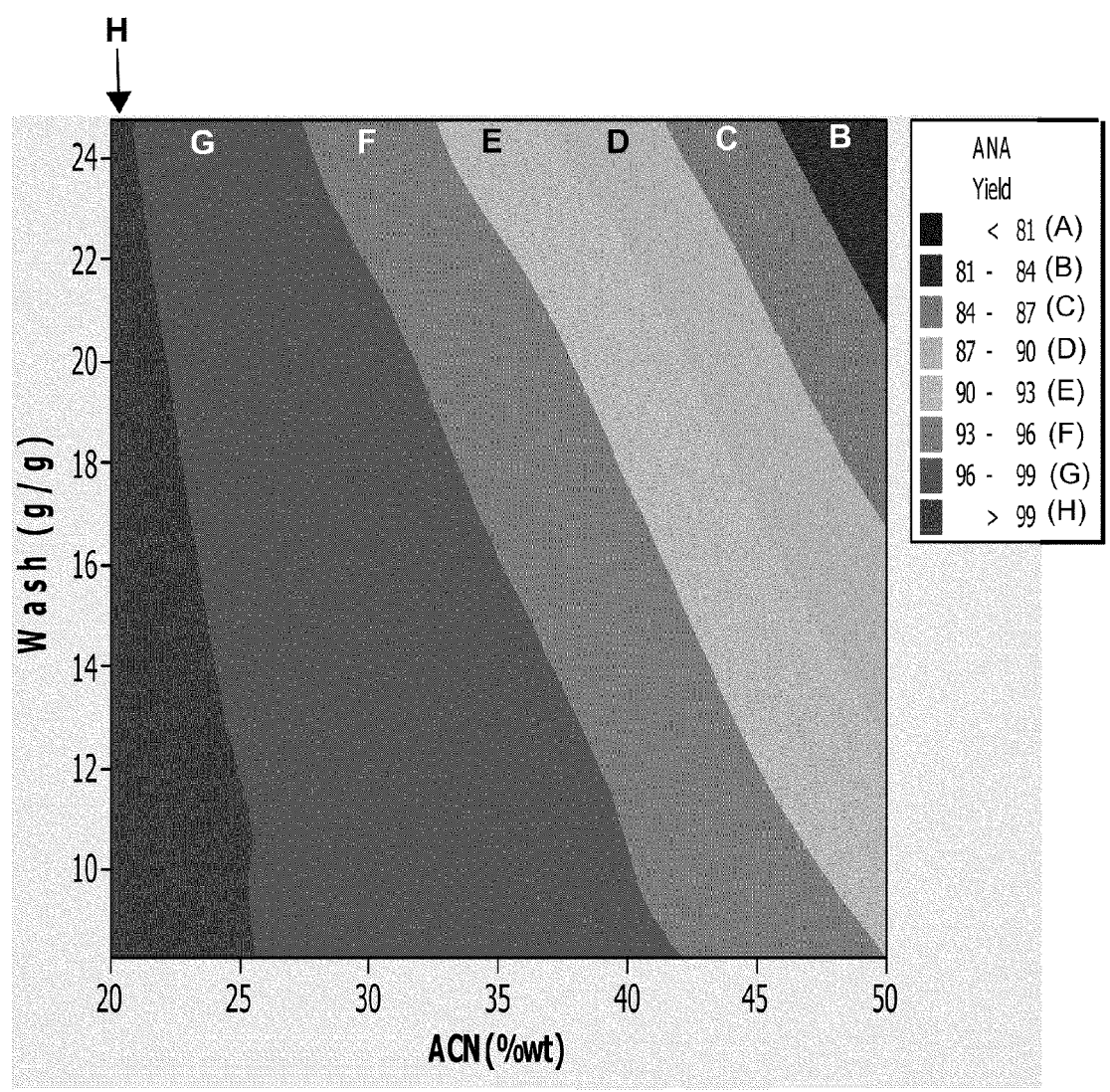
FIG. 10 is a contour plot summarizing the effects of wash ratio and acetonitrile wash solvent concentration on the yield of the resulting noscapine product.
Figure 11:
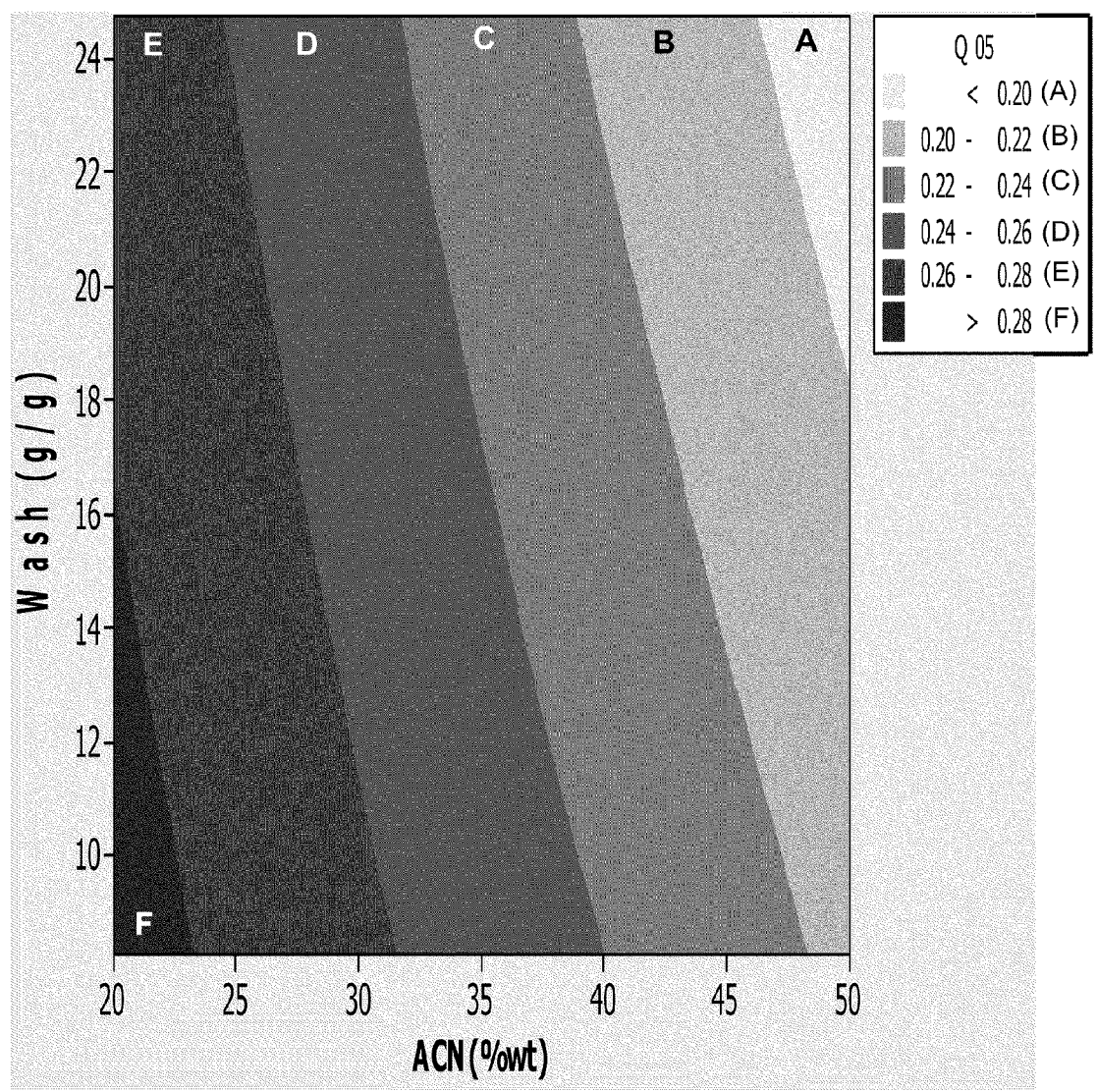
FIG. 11 is a contour plot summarizing the effects of wash volume and acetonitrile wash solvent concentration on the concentration of narcotoline impurities remaining in the purified noscapine product.

Purification of the noscapine improved with higher acetonitrile concentrations and with higher solvent-to-noscapine wash ratios, as shown in FIG. 10. Noscapine yields, which ranged from about 80% to 95%, were also lowest under conditions of high acetonitrile concentration and high solvent-to-noscapine wash ratio, as shown in FIG. 10. The results of this experiment indicated a clear trade-off between yield and purity with respect to the acetonitrile concentrations and wash ratios used in the slurry-washing method. The concentration of narcotoline impurities in the noscapine product was lowest under conditions of high acetonitrile concentration and high solvent-to-noscapine wash ratio, as shown in FIG. 11.

The results of this experiment characterized the sensitivity of the purity, yield, and impurity concentrations to variations in acetonitrile concentration and solvent-to-noscapine wash ratio during slurry-washing of CPS with acetonitrile/H$_2$O solutions. The experimental results highlighted a tradeoff between the yield and the purity of the noscapine product. The most effective reduction of narcotoline impurities occurred at similar conditions to those resulting in the noscapine product with the highest purity, but the lowest yield.

Example 9

Concentrated Poppy Straw Purification Using an Acetonitrile/Water Wash at a pH of 13

To assess the impact of pH on the effectiveness of a acetonitrile/water wash method of noscapine purification, the following experiment was conducted. The CPS described in Example 8 was slurry-washed with an acetonitrile/water solvent in which the concentration of the acetonitrile was 50% by weight, and in which the pH was adjusted to a value of 13 by adding a 50% sodium hydroxide solution, for 15 minutes.

The resulting noscapine had a yield of approximately 85% of the noscapine contained in the CPS, which was slightly lower than the noscapine yield using the method of Example 8, in which the pH was not adjusted. Further, the purity of the resulting noscapine was comparable to that of the noscapine produced using the method of Example 8.

The results of this experiment indicated that adjusting the pH of the acetonitrile/water wash to a value of 13 slightly decreased the yield, and had negligible effect on the noscapine purity relative to the noscapine resulting from an acetonitrile/water wash at an unadjusted pH.

Example 10

Concentrated Poppy Straw Purification Using an Acetonitrile/Water Wash at 50° C.

To assess the impact of temperature on the effectiveness of a acetonitrile/water wash method of noscapine purification, the following experiment was conducted. The CPS described in Example 8 was slurry-washed with an acetonitrile/water solvent in which the concentration of the acetonitrile was 50% by weight, at a temperature of 50° C. for 15 minutes. The mixture was then slowly cooled down to room temperature.

The resulting noscapine had a yield of approximately 87% of the noscapine contained in the CPS, which was slightly lower than the noscapine yield using the method of Example 8 at room temperature. Further, the purity of the resulting noscapine was comparable to that of the noscapine produced using the method of Example 8 at room temperature.

The results of this experiment indicated that conducting the acetonitrile/water wash at 50° C., then allowing the mixture to cool to room temperature slightly decreased the yield, and had negligible effect on the noscapine purity relative to the noscapine resulting from an acetonitrile/water wash at room temperature throughout the purification.

Example 11

Concentrated Poppy Straw Purification Using an Acetone/Water Wash

To assess the effectiveness of a acetone/water wash method of noscapine purification, the following experiment was conducted. The CPS described in Example 8 was slurry-washed with acetone/water solvent in which the concentration of the acetonitrile ranged from about 20% to about 50% by weight. The wash ratios of the slurry-wash varied from 8.25 g to 24.75 g of wash solvent per gram of noscapine, at a temperature of 50° C. for 15 minutes. The mixture was then cooled down to room temperature.

Purification using the acetone/water wash method was most effective at highest acetone concentration and with the highest solvent-to-noscapine wash ratio (results not shown). Noscapine yields, which ranged from 93% to 100%, were also lowest under these same conditions (results not shown). Like the acetonitrile/water wash method described in Example 8, there was a trade-off between the purification conditions that maximized noscapine yield and those conditions that resulted in noscapine with the highest purity.

The results of this experiment indicated that the acetone/water wash method was an effective method of noscapine purification. Compared to the acetonitrile/water wash method described in Example 10, the acetone/water wash method was less effective for the removal of both color and other impurities, but also resulted in higher yields.

Example 12

Concentrated Poppy Straw Purification Using an Acetone/Water Wash at 50° C.

To assess the impact of temperature on the effectiveness of a acetone/water wash method of noscapine purification, the following experiment was conducted. The CPS described in Example 8 was slurry-washed with an acetone/water solvent in which the concentration of the acetone was 50% by weight, at a temperature of 50° C. for 15 minutes. The mixture was then slowly cooled down to room temperature.

The resulting noscapine had a yield of approximately 95% of the noscapine contained in the CPS, which was slightly lower than the noscapine yield using the method of Example 11 at room temperature. Further, the purity of the resulting noscapine was slightly higher than the noscapine produced using the method of Example 11 at room temperature.

The results of this experiment indicated that conducting the acetone/water wash at 50° C., then allowing the mixture to cool to room temperature slightly decreased the yield, and slightly enhanced the noscapine purity relative to the noscapine resulting from an acetone/water wash at room temperature throughout the purification described in Example 11. The method of this experiment was also slightly more effective at eliminating the narcotoline impurities; in this experiment narcotoline impurities were reduced to a concentration of about 0.15%.

Example 13

Purification of Concentrated Poppy Straw Using Dissolution in Acetonitrile Followed by Crystallization with Water To determine the effectiveness of a method of acetone dissolution/water crystallization method at removing impurities from a crude noscapine source, the following experiment was conducted. Concentrated poppy straw (CPS) similar to that described in Example 8 was obtained. The CPS was dissolved in pure acetonitrile at a temperature of 50° C. and to a concentration of 116 mg of noscapine per gram of acetonitrile. After slowly cooling the filtrate to room temperature, an amount of water roughly equal to the amount of acetonitrile was added to the mixture to recrystallize the noscapine. The resulting noscapine crystals were filtered and rinsed with a 30% isopropyl alcohol solution.

The noscapine product resulting from this experiment was nearly white, and nearly 100% pure. The overall yield of the process of this experiment was about 87%, and narcotoline impurities were reduced to a final concentration of about 0.05%.

The results of this experiment demonstrated that acetonitrile extraction followed by water recrystallization was an effective noscapine purification method for the CPS used in this experiment.

Example 14

Purification of Concentrated Poppy Straw Using Dissolution in Acetone Followed by Crystallization with Water To determine the effectiveness of a method of acetone dissolution/water crystallization method at removing impurities from a crude noscapine source, the following experiment was conducted. Concentrated poppy straw (CPS) similar to that described in Example 8 was obtained. The CPS was dissolved in pure acetone at a temperature of 50° C. to a concentration of 116 mg of noscapine per gram of acetone. After slowly cooling the filtrate to room temperature, an amount of water roughly equal to the amount of acetone was added to the mixture to recrystallize the noscapine. The resulting noscapine crystals were filtered and rinsed with a 30% isopropyl alcohol solution.

The noscapine product resulting from this experiment was nearly white, and nearly 100% pure. The overall yield of the process of this experiment was about 95%, and narcotoline impurities were reduced to a final concentration of about 0.06%.

The results of this experiment demonstrated that acetone extraction followed by water recrystallization was an effective noscapine purification method for the CPS used in this experiment.

Example 15

Assessment of the Effectiveness of Noscapine Purification Methods

To assess the effectiveness of a various purification methods at removing impurities from a crude noscapine source, the following experiment was conducted. Concentrated poppy straw (CPS) similar to that described in Example 8 was obtained. The untreated CPS was analyzed for impurities using HPLC methods described in Example 2. HPLC was also used to assess the levels of impurities in the noscapine resulting from the processing of CPS by acetonitrile/water wash (Example 10), acetonitrile dissolution/water recrystallization (Example 13), and acetone dissolution/water recrystallization (Example 14). The results of the HPLC measurements are summarized in Table 4 and Table 5.

TABLE 4

Impurities in noscapine remaining after purification.

| Process | Unknown Impurity Content (% wt of sample) | | | | | | |
|---|---|---|---|---|---|---|---|
| | #2 | #4 | #5 | #6 | #7 | #8 | #9 |
| Untreated CPS | 0.024 | 0.061 | 0.492 | 0.564 | 0.302 | 0.371 | 0.180 |
| Acetonitrile/water wash | 0.024 | 0.034 | 0.230 | 0.122 | 0.061 | 0.154 | 0.075 |

TABLE 4-continued

Impurities in noscapine remaining after purification.

| Process | Unknown Impurity Content (% wt of sample) | | | | | | |
|---|---|---|---|---|---|---|---|
| | #2 | #4 | #5 | #6 | #7 | #8 | #9 |
| ACN dissolution/ water recrystallization | 0.010 | 0.013 | 0.046 | 0.000 | 0.000 | 0.000 | 0.000 |
| Acetone dissolution/ water recrystallization | 0.018 | 0.016 | 0.056 | 0.000 | 0.000 | 0.000 | 0.000 |

TABLE 5

Reduction of impurities in noscapine resulting from various purification processes.

| Process | Reduction of Impurity (% of untreated CPS content) | | | | | | |
|---|---|---|---|---|---|---|---|
| | #2 | #4 | #5 | #6 | #7 | #8 | #9 |
| Untreated CPS | — | — | — | — | — | — | — |
| Acetonitrile/water wash | 0 | 44 | 53 | 78 | 80 | 58 | 58 |
| ACN dissolution/ water recrystallization | 58 | 79 | 91 | 100 | 100 | 100 | 100 |
| Acetone dissolution/ water recrystallization | 25 | 74 | 89 | 100 | 100 | 100 | 100 |

Only seven of the nine potentially important unknown impurity peaks previously identified in Example 2 were detected in the CPS described in Example 8. The quantities of these seven detected impurities in the CPS before and after treatment with various purification methods are listed in Table 4. The overall reduction of each unknown impurity as a percentage of the original amount found in the untreated CPS is listed in Table 5 for each combination of purification methods.

In purification experiments, the unknown impurity #5, later determined to be narcotoline, was found to be the most important impurity to assess overall impurity removal (data not shown). The most effective methodology for the removal of unknown impurity #5 removal was solvent dissolution and recrystallization in water, using either acetonitrile or acetone as the solvent, which resulted in 91% and 89% removal respectively, as shown in Table 5.

The results of this experiment determined the effectiveness of various purification methods at removing the unknown impurities from noscapine extracted from the CPS described in Example 8.

We claim the following:

1. A method for separating noscapine from an opium source comprising at least one impurity that undergoes an irreversible color change when exposed to a pH of less than about 5, the method comprising:
   (a) contacting the opium source with a first solvent that substantially causes the dissolution of noscapine to form a reaction mixture comprising a pH of greater than about 5; and,
   (b) contacting the reaction mixture with a second solvent that reduces the solubility of the noscapine in the reaction mixture without substantially changing the solubility of the impurity such that the noscapine recrystallizes thereby separating the noscapine from the impurity in a manner that does not cause an irreversible color change in the impurity.

2. The method of claim 1, wherein the first solvent is selected from the group consisting of alkane and substituted alkane solvents, aromatic hydrocarbons, esters, ethers, ketones, and combinations thereof.

3. The method of claim 1, wherein the first solvent is selected from the group consisting of acetonitrile, acetone, benzene, butanol, butyl acetate, t-butyl methylether, t-butyl methylketone, chlorobenzene, chloroform, chloromethane, cyclohexane, dichloromethane, dichloroethane, diethyl ether, ethyl acetate, fluorobenzene, heptane, hexanes, isobutylmethylketone, isopropyl acetate, methylethylketone, methylisobutylketone, methyltetrahydrofuran, pentyl acetate, n-propyl acetate, tetrahydrofuran, toluene, and combinations thereof; and the second solvent is selected from the group consisting of water, methanol, ethanol, isopropanol, pentanol, and combinations thereof.

4. The method of claim 1, wherein the impurity is selected from the group consisting of papaverrubines, glaudine, epiglaudine, oreodine, and combinations thereof.

5. The method of claim 4, wherein the papaverrubine is selected from the group consisting of papaverrubine A, papaverrubine B, papaverrubine C, papaverrubine D, papaverrubine E, papaverrubine F, papaverrubine G, epipapaverrubine G, papaverrubine H, and combinations thereof.

6. The method of claim 1, wherein the opium source comprises at least one other impurity selected from the group consisting of morphine, oripavine, papaverine, thebaine, codeine, codeine, cryptopine, noscapine analog, narcotoline, nor-noscapine, and combinations thereof.

7. The method of claim 1, wherein the opium source is selected from the group consisting of poppy straw, concentrated poppy straw, opium, crude noscapine, and crude narcotine.

8. The method of claim 1, wherein the noscapine crystals remain a tan color before and after separation from the opium source.

9. The method of claim 1, wherein the concentration of noscapine in the reaction mixture in step (a) ranges between about 10% to about 90% of the solubility limit of noscapine in the first solvent; and the amount of the second solvent contacted with the reaction mixture is sufficient to reduce the solubility of the noscapine in the reaction mixture by a factor of at least about 10% or less of the solubility of the reaction mixture before contacting the second solvent.

10. The method of claim 1, wherein step (a) of the method is conducted at a temperature ranging between about 50° C. and the boiling point of the first solvent, and step (b) is conducted at a temperature ranging between about 20° C. and the eutectic temperature of the combined first solvent and second solvent from step (b).

11. The method of claim 1, wherein the second solvent is miscible with the first solvent.

12. The method of claim 1, wherein the method further comprises:
  (a) filtering the crystallized noscapine; and,
  (b) rinsing the filtered noscapine product with a rinse solvent.

13. The method of claim 12, wherein the rinse solvent is a mixture of water and a second rinse solvent selected from the group consisting of methanol, ethanol, isopropanol, pentanol, acetonitrile, acetone, and combinations thereof.

14. A method for separating noscapine from an opium source comprising at least one impurity that undergoes an irreversible color change when exposed to a pH of less than about 5, the method comprising:
  (a) contacting the opium source with a first solvent selected from the group consisting of acetone, acetonitrile, and combinations thereof to form a reaction mixture having a pH of greater than about 5; and,
  (b) contacting the reaction mixture with water such that the noscapine recrystallizes thereby separating the noscapine from the impurity.

15. The method of claim 14, wherein step (a) of the method is conducted at a temperature ranging between about 40° C. and about 60° C.; step (b) is conducted at a temperature of between about 0° C. and about 25° C.; the concentration of noscapine in the reaction mixture in step (a) ranges between about 10% and about 20% by weight; and the amount of water added to the reaction mixture in step (b) is essentially equal to the volume of the first solvent in the reaction mixture.

16. The method of claim 14, wherein the opium source is concentrated poppy straw.

17. The method of claim 14, wherein the method further comprises filtering the reaction mixture from step (b).

18. The method of claim 14, wherein the impurity is selected from the group consisting of papaverrubines, glaudine, epiglaudine, oreodine, and combinations thereof.

19. The method of claim 14, wherein the opium source further comprises at least one other impurity selected from the group comprising morphine, oripavine, papaverine, thebaine, codeine, codeine, cryptopine, noscapine analog, narcotoline, nor-noscapine, and combinations thereof.

20. The method of claim 14, wherein the noscapine crystals comprise a purity of at least 98% noscapine by weight; and noscapine crystals comprise a yield of at least 80% of the noscapine by weight of the opium source.

* * * * *